US010376420B2

(12) United States Patent
Chandrasekaran et al.

(10) Patent No.: US 10,376,420 B2
(45) Date of Patent: Aug. 13, 2019

(54) PERSONAL HYGIENE ARTICLE AND CONTAINER FOR THE SAME

(71) Applicant: 3M INNOVATIVE PROPERTIES COMPANY, St. Paul, MN (US)

(72) Inventors: Neelakandan Chandrasekaran, Woodbury, MN (US); Robert L. W. Smithson, Mahtomedi, MN (US); Leigh E. Wood, Woodbury, MN (US); Timothy V. Stagg, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 539 days.

(21) Appl. No.: 14/897,989

(22) PCT Filed: Jun. 12, 2014

(86) PCT No.: PCT/US2014/042075
§ 371 (c)(1),
(2) Date: Dec. 11, 2015

(87) PCT Pub. No.: WO2014/201221
PCT Pub. Date: Dec. 18, 2014

(65) Prior Publication Data
US 2016/0136002 A1 May 19, 2016

Related U.S. Application Data

(60) Provisional application No. 61/978,122, filed on Apr. 10, 2014, provisional application No. 61/834,690, filed on Jun. 13, 2013.

(51) Int. Cl.
*A61F 13/15* (2006.01)
*A61F 13/511* (2006.01)
(Continued)

(52) U.S. Cl.
CPC .. *A61F 13/15203* (2013.01); *A61F 13/15707* (2013.01); *A61F 13/513* (2013.01);
(Continued)

(58) Field of Classification Search
CPC .......... A61F 13/15203; A61F 13/15707; A61F 13/5113; A61F 13/513; A61F 13/51394;
(Continued)

(56) References Cited

U.S. PATENT DOCUMENTS 3,930,502 A 1/1976 Tritsch
4,435,141 A 3/1984 Weisner
(Continued)

FOREIGN PATENT DOCUMENTS

DE 3831580 4/1989
EP 0341993 11/1989
(Continued)

OTHER PUBLICATIONS

US 5,389,416 A, 02/1995, Mody (withdrawn)
(Continued)

*Primary Examiner* — Jacqueline F Stephens (57) ABSTRACT

A personal hygiene article includes a chassis with a topsheet, a backsheet, and an absorbent component between the topsheet and the backsheet. At least one portion of the personal hygiene article includes a microporous film having an opaque, microporous region and at least one see-through region of lower porosity within the opaque, microporous region. The microporous film can include a beta-nucleating agent or can have thermally induced phase separation caused by a diluent. A container includes a microporous film enclosing at least one personal hygiene article. The microporous film has an opaque, microporous region and at least one see-through region of lower porosity forming a window
(Continued)

within the opaque, microporous region. Methods of making the personal hygiene article and container are also described.

18 Claims, 3 Drawing Sheets

(51) Int. Cl.
*A61F 13/513* (2006.01)
*A61F 13/514* (2006.01)
*A61F 13/551* (2006.01)
*A61F 13/84* (2006.01)

(52) U.S. Cl.
CPC .. *A61F 13/51113* (2013.01); *A61F 13/51394* (2013.01); *A61F 13/51496* (2013.01); *A61F 13/551* (2013.01); *A61F 13/84* (2013.01); *A61F 2013/15243* (2013.01); *A61F 2013/15715* (2013.01); *A61F 2013/51147* (2013.01); *A61F 2013/8402* (2013.01); *A61F 2013/8497* (2013.01)

(58) Field of Classification Search
CPC .. A61F 13/51496; A61F 13/551; A61F 13/84; A61F 2013/15243; A61F 2013/15715; A61F 2013/51147; A61F 2013/8402; A61F 2013/8497; B32B 3/30
USPC ............. 604/389, 362, 367, 383, 385.03
See application file for complete search history.

(56) References Cited

U.S. PATENT DOCUMENTS

| | | |
|---|---|---|
| 4,609,584 A | 9/1986 | Cutler |
| 4,775,310 A | 10/1988 | Fischer |
| 4,839,131 A | 6/1989 | Cloeren |
| 4,894,060 A | 1/1990 | Nestegard |
| 4,902,553 A | 2/1990 | Hwang |
| 4,923,650 A | 5/1990 | Antoon, Jr. et al. |
| 5,120,594 A | 6/1992 | Mrozinski |
| 5,236,963 A | 8/1993 | Jacoby et al. |
| 5,256,231 A | 10/1993 | Gorman |
| 5,387,207 A * | 2/1995 | Dyer .................. A61F 5/4401 521/64 |
| 5,491,188 A | 2/1996 | Ikeda |
| 5,510,161 A | 4/1996 | Lloyd |
| 5,516,567 A | 5/1996 | Roessler et al. |
| 5,569,234 A * | 10/1996 | Buell ............... A61F 13/49009 604/396 |
| 5,572,291 A | 11/1996 | Moriguchi |
| 5,845,375 A | 12/1998 | Miller |
| 5,868,987 A | 2/1999 | Kampfer |
| 5,897,541 A | 4/1999 | Uitenbroek |
| 5,953,797 A | 9/1999 | Provost |
| 6,075,179 A | 6/2000 | McCormack |
| 6,110,588 A | 8/2000 | Perez |
| 6,132,660 A | 10/2000 | Kampfer |
| 6,190,594 B1 | 2/2001 | Gorman |
| 6,190,758 B1 | 2/2001 | Stopper |
| 6,240,817 B1 | 6/2001 | James et al. |
| 6,287,665 B1 | 9/2001 | Hammer |
| 6,334,504 B1 | 1/2002 | Sato |
| 6,368,097 B1 | 4/2002 | Miller |
| 6,368,742 B2 | 4/2002 | Fisher |
| 6,420,024 B1 | 7/2002 | Perez |
| 6,544,633 B1 | 4/2003 | Ogura |
| 6,586,073 B2 | 7/2003 | Perez |
| 6,627,133 B1 | 9/2003 | Tuma |
| 6,632,850 B2 | 10/2003 | Hughes |
| 6,669,887 B2 | 12/2003 | Hilston |
| 6,708,378 B2 | 3/2004 | Parellada |
| 6,719,742 B1 | 4/2004 | McCormack |
| 6,815,048 B2 | 11/2004 | Davidson |
| 6,861,132 B2 | 3/2005 | Ikeda et al. |
| 7,168,139 B2 | 1/2007 | Seth |
| 7,185,761 B2 | 3/2007 | Molina |
| 7,198,743 B2 | 4/2007 | Tuma |
| 7,214,334 B2 | 5/2007 | Jens |
| 7,220,478 B2 | 5/2007 | McCormack |
| 7,423,088 B2 | 9/2008 | Mäder |
| 7,682,689 B2 | 3/2010 | Sadamitsu et al. |
| 7,875,012 B2 | 1/2011 | Arco |
| 7,897,078 B2 | 3/2011 | Petersen |
| 8,191,709 B2 | 6/2012 | Molina |
| 8,324,444 B2 | 12/2012 | Hansson |
| 8,613,736 B2 | 12/2013 | Schnabel |
| 8,680,169 B2 | 3/2014 | Yamada |
| 9,278,471 B2 | 3/2016 | Chandrasekaran |
| 9,358,714 B2 | 6/2016 | Chandrasekaran |
| 2002/0062117 A1 | 5/2002 | Raufman |
| 2003/0035943 A1 | 2/2003 | Jones |
| 2003/0091617 A1 | 5/2003 | Mrozinski |
| 2003/0091618 A1 | 5/2003 | Seth |
| 2003/0148091 A1 | 8/2003 | Ikeda et al. |
| 2003/0207137 A1 | 11/2003 | Kong et al. |
| 2004/0209063 A1 | 10/2004 | Gallagher et al. |
| 2005/0215963 A1 | 9/2005 | Autran et al. |
| 2005/0288510 A1 | 12/2005 | Mader et al. |
| 2006/0024520 A1 * | 2/2006 | Kong .................. B32B 3/26 428/517 |
| 2006/0177632 A1 | 8/2006 | Jacoby |
| 2007/0020448 A1 | 1/2007 | Hubbard |
| 2007/0082154 A1 | 4/2007 | Ambroise |
| 2007/0286976 A1 | 12/2007 | Selen |
| 2008/0000581 A1 | 1/2008 | Nison |
| 2008/0000793 A1 | 1/2008 | Messerschmidt et al. |
| 2008/0233373 A1 | 9/2008 | Coburn |
| 2009/0258212 A1 | 10/2009 | Jacoby |
| 2009/0258560 A1 | 10/2009 | Kristiansen |
| 2010/0010168 A1 | 1/2010 | Wolfschwenger et al. |
| 2010/0301510 A1 | 12/2010 | Coburn |
| 2011/0088828 A1 | 4/2011 | Misek |
| 2011/0147475 A1 | 6/2011 | Biegler |
| 2011/0151171 A1 | 6/2011 | Biegler |
| 2011/0264064 A1 | 10/2011 | Arora |
| 2012/0220973 A1 | 8/2012 | Chan |
| 2012/0242009 A1 | 9/2012 | Mullane |
| 2012/0308755 A1 | 12/2012 | Gorman |
| 2012/0329647 A1 | 12/2012 | Nellenbach |
| 2013/0202828 A1 | 8/2013 | Jacoby |
| 2014/0044934 A1 | 2/2014 | Bills |
| 2014/0093716 A1 | 4/2014 | Hanschen |
| 2016/0278987 A1 | 9/2016 | Chandrasekaran |

FOREIGN PATENT DOCUMENTS

| | | |
|---|---|---|
| EP | 0539504 | 5/1993 |
| EP | 0581323 | 2/1994 |
| EP | 0925769 | 6/1999 |
| EP | 0974326 | 2/2000 |
| EP | 1816158 | 8/2007 |
| GB | 2252838 | 8/1992 |
| GB | 2252839 | 8/1992 |
| GB | 2323325 | 9/1998 |
| GB | 2323327 | 9/1998 |
| JP | 06033022 | 2/1994 |
| JP | 10-85257 | 4/1998 |
| JP | 10114357 | 5/1998 |
| JP | 2000169608 | 6/2000 |
| JP | 2002-315607 | 10/2002 |
| JP | 3414494 | 6/2003 |
| JP | 2004331944 | 11/2004 |
| JP | 2005-279005 | 10/2005 |
| JP | 2006-314361 | 11/2006 |
| WO | WO 93/19714 | 10/1993 |
| WO | WO 1994-06387 | 3/1994 |
| WO | WO 9605262 | 2/1996 |
| WO | WO 96-10380 | 4/1996 |
| WO | WO 2002-081557 | 10/2002 |
| WO | WO 03/086257 | 10/2003 |
| WO | WO 2003-093004 | 11/2003 |
| WO | WO 2004-075803 | 9/2004 |
| WO | WO 2005-004777 | 1/2005 |

(56) References Cited

FOREIGN PATENT DOCUMENTS

| WO | WO 2006-023442 | 3/2006 |
|---|---|---|
| WO | WO 2006-073919 | 7/2006 |
| WO | WO 2007-032965 | 3/2007 |
| WO | WO 2009-040767 | 4/2009 |
| WO | WO 2010-065602 | 6/2010 |
| WO | WO 2011-119323 | 9/2011 |
| WO | WO 2013-152287 | 10/2013 |
| WO | WO 2014-201219 | 12/2014 |
| WO | WO 2014-201229 | 12/2014 |

OTHER PUBLICATIONS

Chu, "Crystal transformation and micropore formation during uniaxial drawing of β-form polypropylene film", *Polymer*, 1995, vol. 36, No. 13, pp. 2523-2530.

Chu, "Microvoid formation process during the plastic deformation of β-form polypropylene", *Polymer*, 1994, vol. 35, No. 16, pp. 3442-3448.

Jones, "Crystalline forms of isotactic polypropylene", 1964, vol. 75, No. 1, pp. 134-158.

International Search report for PCT International Application No. PCT/US2014/042075 dated Oct. 2, 2014, 3pages.

\* cited by examiner

PERSONAL HYGIENE ARTICLE AND CONTAINER FOR THE SAME

CROSS-REFERENCE TO RELATED APPLICATION

This application is a national stage filing under 35 U.S.C. 371 of PCT/US2014/042075 filed Jun. 12, 2014, which claims priority to U.S. Application Nos. 61/834,690, filed Jun. 13, 2013, and 61/978,122, filed Apr. 10, 2014, the disclosures of which are incorporated by reference in their entirety herein.

BACKGROUND

A variety of different personal hygiene articles (e.g., absorbent articles such as diapers, adult incontinence products, and sanitary napkins) that include different printed and/or colored regions are available in the market. Printing or coloring on such articles can be attractive to the consumer and help the consumer differentiate between different brands. Some manufacturers of absorbent articles print with multi-colored graphics that are a signature of their brand. Others may use monochromatic printing on the articles. Printing approaches to providing a differentiated product generally use ink, colored adhesives, or heat- or pressure-activated chemical colorants, each of which adds cost to the product that is passed on to consumers. Some recent examples of absorbent articles with patterns or colors include those described in U.S. Pat. No. 8,324,444 (Hansson et al.) and U.S. Pat. Appl. Pub. Nos. 2011/0264064 (Arora et al.) and 2012/0242009 (Mullane et al.). Packages for personal hygiene articles having windows are reported in U.S. Pat. No. 8,191,709 (Molina et al.).

SUMMARY

The present disclosure provides a personal hygiene article and a container for personal hygiene articles, in which the personal hygiene article or the container includes a microporous film. The microporous film has an opaque, microporous region and at least one see-through region of lower porosity within the opaque, microporous region. The see-through region of lower porosity has a predetermined (in other words, designed) shape. Advantageously, the see-through region can be in the form of a wide variety of patterns, numbers, pictures, symbols, alphabetical letters, bar code, or combinations thereof that can be selected to be aesthetically pleasing to a user. The see-through region can also be in the form of a company name, brand name, or logo that may be readily identified by a customer. The personal hygiene article or container according to the present disclosure can be readily customized depending on the requirements of a particular product. The see-through region provides a visual image without the use of inks or other expensive, color-providing chemicals. The see-through region in the container allows the consumer to see the thickness and color of the personal hygiene articles within.

In one aspect, the present disclosure provides a personal hygiene article. The personal hygiene article includes a chassis with a topsheet, a backsheet, and an absorbent component between the topsheet and the backsheet. At least one portion of the personal hygiene article includes a microporous film having an opaque, microporous region and at least one see-through region of lower porosity within the opaque, microporous region. The microporous film comprises a beta-nucleating agent or has thermally induced phase separation caused by a diluent. For example, at least one of the topsheet, the backsheet, an acquisition layer between the topsheet and the backsheet, a side panel attached along at least a portion of a first or second opposing longitudinal edge, an ear attached along at least a portion of the first or second opposing longitudinal edge, or a loop tape on the backsheet can include the microporous film having an opaque, microporous region and at least one see-through region of lower porosity within the opaque, microporous region.

In another aspect, the present disclosure provides a container including a microporous film. The container encloses at least one personal hygiene article. The microporous film has an opaque, microporous region and at least one see-through region of lower porosity forming a window within the opaque, microporous region.

In another aspect, the present disclosure provides a method of making the personal hygiene article or the container. The method includes providing a microporous film, collapsing some pores in the microporous film to form at least one see-through region of lower porosity within an opaque, microporous region of the microporous film, and assembling at least a portion of the microporous film including the at least one see-through region of lower porosity and the opaque, microporous region into the personal hygiene article or into the container.

In another aspect, the present disclosure provides a method of making the personal hygiene article described above. The method includes providing a microporous film, collapsing some pores in the microporous film to form at least one see-through region of lower porosity within an opaque, microporous region of the microporous film, and assembling at least a portion of the microporous film including the at least one transparent region of lower porosity and the opaque, microporous region into the personal hygiene article.

In another aspect, the present disclosure provides a method of making the container described above. The method includes providing a microporous film, collapsing some pores in the microporous film to form the at least one see-through region of lower porosity within the opaque, microporous region of the microporous film, assembling the microporous film into the container enclosing the at least one personal hygiene article.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure in their relative sense only. It will be understood that, unless otherwise noted, those terms are used merely as a matter of convenience in the description of one or more of the embodiments.

The term "microporous" refers to having multiple pores that have an average dimension (in some cases, diameter) of up to 10 micrometers. At least some of the multiple pores should have a dimension on the order of or larger than the wavelength of visible light. For example, at least some of the pores should have a dimension (in some cases, diameter) of at least 400 nanometers. Pore size is measured by measuring bubble point according to ASTM F-316-80. The pores may be open cell pores or closed cell pores. In some embodiments, the pores are closed cell pores.

The term "see-through" refers to either transparent (that is, allowing passage of light and permitting a clear view of objects beyond) or translucent (that is, allowing passage of light and not permitting a clear view of objects beyond). The see-through region may be colored or colorless. It should be understood that a "see-through" region is large enough to be seen by the naked eye.

The term "within" with regard to the at least one see-through region with the opaque, microporous region means that the opaque, microporous region may border the at least one see-through region on at least two sides or more. In some embodiments, the opaque, microporous region surrounds the at least one see-through region. Generally, the at least one see-through region is not found only at the edge of the microporous film.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
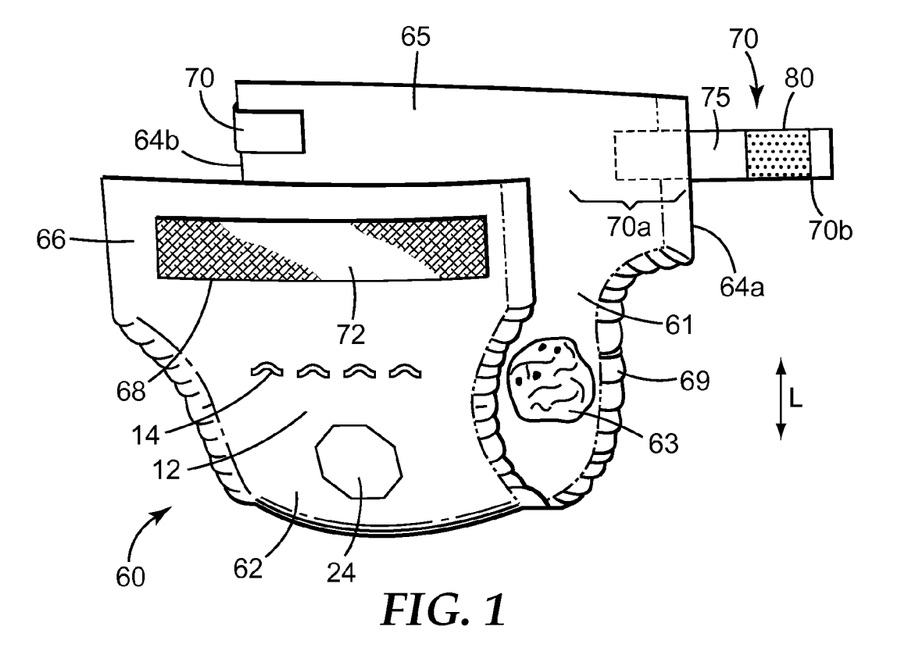
FIG. 1 is a perspective view of an embodiment of a personal hygiene article according to the present disclosure.

FIG. 1 is a perspective view of an embodiment of a personal hygiene article according to the present disclosure. The personal hygiene article is a diaper 60 having an essentially hourglass shape. The diaper comprises an absorbent core 63 between a liquid permeable top sheet 61 that contacts the wearer's skin and an outwardly facing liquid impermeable backsheet 62. Diaper 60 has a rear waist region 65 having two fastening tabs 70 arranged at the two longitudinal edges 64a, 64b of diaper 60. Fastening tab 70 has a manufacturer's end 70a secured to the diaper rear waist region 65 and a user's end 70b. The diaper 60 may comprise an elastic material 69 along at least a portion of longitudinal side edges 64a and 64b to provide leg cuffs. When attaching the diaper 60 to a wearer's body, the user's ends 70b of fastening tabs 70 can be attached to a target area 68 comprising fibrous material 72 arranged on the backsheet 62 of the front waist region 66. The longitudinal direction "L" of the personal hygiene article (e.g., diaper 60) refers to the direction that the article extends from the front to rear of the user. Therefore, the longitudinal direction refers to the length of the personal hygiene article between the rear waist region 65 and the front waist region 66. The lateral direction of the personal hygiene article (e.g., diaper 60) refers to the direction that the article extends from the left side to the right side (or vice versa) of the user (i.e., from longitudinal edge 64a to longitudinal edge 64b in the embodiment of FIG. 1).

In the embodiment illustrated in FIG. 1, fastening tab 70 comprises a tape backing 75 bearing an adhesive. The adhesive may be useful for joining optional mechanical fastener 80 to the tape backing 75 and joins the tape backing 75 to the rear waist region 65 of the diaper. In the illustrated embodiment, exposed adhesive may be present on the tape backing 75 between the mechanical fastener 80 and the diaper rear waist region 65. Fastening tab 70 further comprises release tape (not shown) to contact the exposed adhesive when the user's end 70b is folded onto diaper rear waist region 65 (e.g., during packaging and shipping of diaper 60 as shown for the fastening tab 70 at longitudinal edge 64b). The release tape may be joined to the tape backing 75 and diaper rear waist region 65 using adhesive although in some embodiments, thermobonding, ultrasonic bonding, or laser bonding may be useful. Various configurations of release tape are possible depending on the configuration of the attachment of the fastening tab 70 to diaper 60. The tape backing 75 at the user's end 70b of the fastening tab 70 may exceed the extension of the adhesive and optional mechanical fastener 80 thereby providing a fingerlift. Examples of loop tapes which may be applied to the target area 68 to provide an exposed fibrous material 72, are disclosed, for example, in U.S. Pat. No. 5,389,416 (Mody et al.) EP 0,341,993 (Gorman et al.) and EP 0,539,504 (Becker et al.). In other embodiments, the backsheet 62 comprises a woven or nonwoven fibrous layer which is capable of interacting with the user's ends 70b of the fastening tabs 70 comprising a hook strip disclosed herein. Examples of such backsheets 62 are disclosed, for example, in U.S. Pat. No. 6,190,758 (Stopper) and U.S. Pat. No. 6,075,179 (McCormack et al.).

In diaper 60, backsheet 62 includes a microporous film having an opaque, microporous region 12 and at least one see-through region of lower porosity 14 within the opaque, microporous region 12. The see-through region of lower porosity 14 is included in a pattern of see-through regions of lower porosity although this is not a requirement. There may be more than one see-through region of lower porosity within the opaque, microporous region that does not necessarily form a repeating pattern. For example, multiple see-through regions in the form of alphabetical letters can be used together to form a word. Backsheet 62 also includes a different see-through region of lower porosity 24 within the opaque, microporous region 12. The see-through region(s) of lower porosity 14 or 24 or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, bar codes, or combination thereof may be part of a company name, logo, brand name, or trademark picture if desired.

Although FIG. 1 illustrates a backsheet 62 including a microporous film having an opaque, microporous region 12 and at least one see-through region of lower porosity 14, 24 within the opaque, microporous region 12, any one or any combination of two or more of the backsheet 62, topsheet 61, fastening tab 70, target area 68 (or landing zone), side panels (not shown), ears (not shown), acquisition layer (not shown), disposal tape (not shown), or mechanical fastener 80 may comprise a microporous film having an opaque, microporous region and at least one see-through region of lower porosity within the opaque, microporous region.

In the personal hygiene article and container according to the present disclosure, the relative areas of the at least one see-through region of lower porosity and the opaque, microporous region may be different in different embodiments. The at least one see-through region of lower porosity can make up at least 5, 10, 20, 25, 50, 75, or 90 percent a given area of the backsheet, topsheet, fastening tab, target area (or landing zone), side panel, ear, acquisition layer, disposal tape, mechanical fastener, or container. For some patterns (e.g., a pattern of rhombuses or other geometric shapes), the opaque microporous region may appear as strands separating the see-through regions. For other patterns, the see-through regions may appear more widely separated on a continuous, opaque, microporous background.

The size of any individual see-through area of lower porosity in the personal hygiene article or container according to the present disclosure may be at least 0.3 mm$^2$, 0.4 mm$^2$, 0.5 mm$^2$, or 0.7 mm$^2$. Generally, if the color contrast between the opaque, microporous region and any underlying layer beneath the any individual see-through area of lower porosity is relatively large, smaller individual see-through areas (e.g., 0.3 mm$^2$ to 0.6 mm$^2$) may be easily visible to the naked eye. However, if the color contrast between the opaque, microporous region and any underlying layer beneath the any individual see-through area of lower porosity is relatively small, it may be desirable to have larger individual see-through areas (e.g., larger than 0.6 mm$^2$).

The various components of a personal hygiene article, such as those described above in connection with FIG. 1, can be made from a variety of suitable materials and assembled together in a variety of ways. In addition to the microporous films having an opaque, microporous region and at least one see-through region of lower porosity within the opaque, microporous region described herein, suitable materials for various components of the personal hygiene article may comprise woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. The term "non-woven" refers to a material having a structure of individual fibers or threads that are interlaid but not in an identifiable manner such as in a knitted fabric. In some embodiments, multiple layers of nonwoven materials including, for example, at least one layer of a meltblown nonwoven and at least one layer of a spunbonded nonwoven, or any other suitable combination of nonwoven materials may be useful. For example, spunbond-meltbond-spunbond, spunbond-spunbond, or spunbond-spunbond-spunbond multilayer material may be useful. Composite web comprising any combination of nonwoven layers and dense film layers may also be useful. Fibrous materials that provide materials for personal hygiene articles may be made of natural fibers (e.g., wood, rayon, or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. The components of a personal hygiene article can be assembled by a variety of methods including adhesive bonding, thermobonding, ultrasonic bonding, laser bonding, compression bonding, or surface bonding.

In personal hygiene articles according to the present disclosure, such as that shown in FIG. 1, the topsheet 61 is typically permeable to liquid and designed to contact a wearer's skin, and the outwardly facing backsheet 62 is typically impermeable to liquids. There is typically an absorbent core 63 encased between the topsheet and the backsheet. Various materials can be useful for the topsheet 61, the backsheet 62, and the absorbent core 63 in an absorbent article according to the present disclosure. Examples of materials useful for topsheets 61 include apertured plastic films, woven fabrics, nonwoven webs, porous foams, and reticulated foams. In some embodiments of the personal hygiene articles according to the present disclosure, at least a portion of the topsheet is made from a microporous film having an opaque, microporous region and at least one see-through region of lower porosity within the opaque, microporous region. In some embodiments, the topsheet 61 is a nonwoven material. Examples of suitable nonwoven materials including any of those described above. The nonwoven web can be surface treated with a surfactant or otherwise processed to impart the desired level of wettability and hydrophilicity. The backsheet 62 is sometimes referred to as the outer cover and is the farthest layer from the user. The backsheet 62 functions to prevent body exudates contained in absorbent core from wetting or soiling the wearer's clothing, bedding, or other materials contacting the diaper. In some embodiments of the personal hygiene articles according to the present disclosure, at least a portion of the backsheet is made from a microporous film having an opaque, microporous region and at least one see-through region of lower porosity within the opaque, microporous region. Such films can provide the advantages of being vapor or gas permeable and substantially impermeable to liquid. Other portions of the backsheet 62 can include other thermoplastic films (e.g., a poly(ethylene) film). The backsheet 62 can also include woven or nonwoven fibrous webs, for example, laminated to the thermoplastic films or constructed or treated to impart a desired level of liquid impermeability even in the absence of a thermoplastic film. The thermoplastic film may be embossed and/or matte finished to provide a more aesthetically pleasing appearance. Suitable absorbent cores 63 include natural, synthetic, or modified natural polymers that can absorb and hold liquids (e.g., aqueous liquids). Such polymers can be crosslinked (e.g., by physical entanglement, crystalline domains, covalent bonds, ionic complexes and associations, hydrophilic associations such as hydrogen bonding, and hydrophobic associations or Van der Waals forces) to render them water insoluble but swellable. Such absorbent materials are usually designed to quickly absorb liquids and hold them, usually without release. Examples of suitable absorbent materials useful in absorbent articles disclosed herein include wood pulp or other cellulosic materials and super absorbent polymers (SAP).

Some personal hygiene articles according to the present disclosure include an acquisition layer, which can be useful for quickly accepting an incoming insult and either absorb, hold, channel, or otherwise manage the liquid so that it does not leak outside the article. The acquisition layer may also be referred to, for example, as an acquisition/distribution layer (ADL), surge layer, intake layer, transfer layer, or transport layer. An acquisition layer is generally capable of handling an incoming insult of between about 60 and 100 milliliters (mL) at an insult volumetric flow rate of from about 5 to 20 mL/second, for infants, for example. An acquisition layer is generally subjacent the topsheet at the surface opposite the user's skin. The acquisition layer can be between the topsheet and the absorbent core, between the absorbent core and the backsheet, or within the absorbent core. Various woven and nonwoven webs and foams can be used to construct an acquisition layer. Acquisition layers may be composed of a substantially hydrophobic material, and the hydrophobic material may optionally be treated with a surfactant or otherwise processed to impart a desired level of wettability and hydrophilicity. In some embodiments of the personal hygiene article according to the present disclosure, the acquisition layer is made from a microporous film having an opaque, microporous region and at least one see-through region of lower porosity within the opaque, microporous region.

As described above, in some embodiments, a component of a personal hygiene article can be surface treated with a surfactant (e.g., in an amount between about 0.05 and 0.5 weight percent). As described above, a surfactant treatment may be useful if the component a topsheet or an acquisition/distribution layer. A surfactant can be applied to the component by any conventional means (e.g., spraying, printing, dipping, or brush coating).

Personal hygiene articles (e.g., incontinence articles and diapers) according to the present disclosure may have any desired shape such as a rectangular shape, a shape like the letter I, a shape like the letter T, or an hourglass shape. The personal hygiene article may also be a pants-style diaper or refastenable pants-style diaper with fastening tabs along each longitudinal edge. In some embodiments, including the embodiment shown in FIG. 1, the topsheet 61 and backsheet 62 are attached to each other and together form chassis all the way out to the first and second longitudinal opposing edges 64a and 64b. In some embodiments, only one of the topsheet 61 or the backsheet 62 extends to the first and second longitudinal opposing edges 64a and 64b. In other embodiments, the chassis can include separate side panels that are attached to the sandwich of at least topsheet 61, backsheet 62, and absorbent core 63 during manufacturing of the absorbent article, for example, to form ear portions. The side panels can be made of a material that is the same as the topsheet 61 or backsheet 62 or may be made from a different material (e.g., a different nonwoven). In these embodiments, the side panels also form part of the chassis. As described above, the side panels or ears can comprise a microporous film having an opaque, microporous region and at least one see-through region of lower porosity within the opaque, microporous region. Also, an absorbent article can have two target zones of loop material along the longitudinal edges of the backsheet instead of the large target area 68 shown in FIG. 1.

Figure 5:
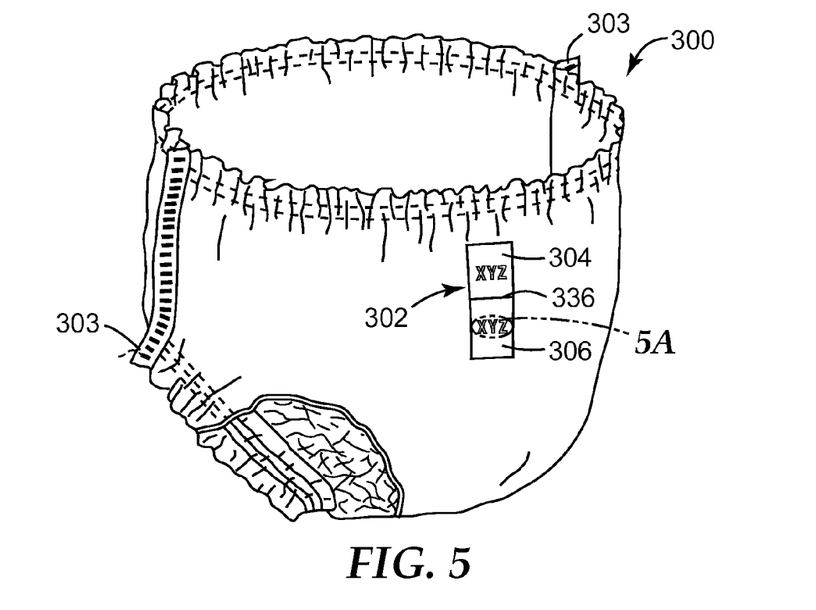
FIG. 5 is a perspective view of another embodiment of personal hygiene article according to the present disclosure, incorporating a disposal tape.
Figure 5A:
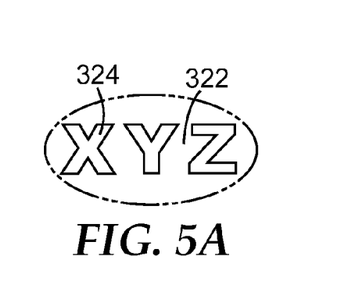
FIG. 5A is an expanded view of the indicated area in FIG. 5.
Figure 5B:
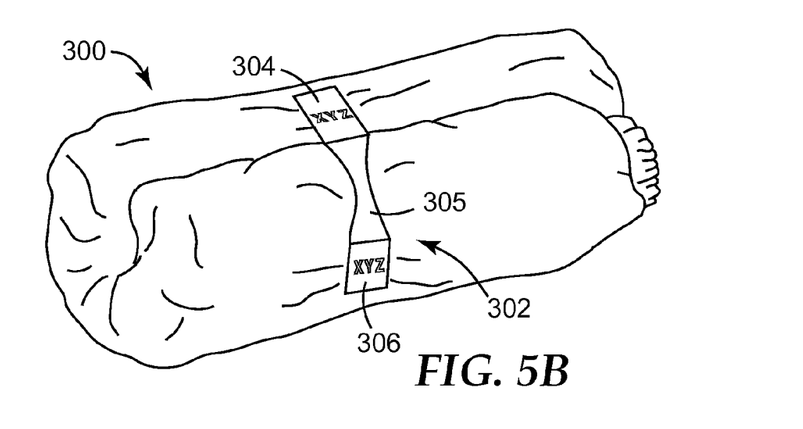
FIG. 5B is a perspective view of the personal hygiene article shown in FIG. 5 rolled up and ready for disposal.

Another embodiment of a personal hygiene article according to the present disclosure is shown in FIGS. 5, 5A, and 5B in connection with a pants or shorts style incontinence article 300, which may be an infant diaper or adult incontinence article. After use of such a pants style incontinence article, it is typically torn apart along at least one of its seams 303 before rolling it up so that it does not have to be removed over the legs. Article 300 has a disposal tape 302 on a portion of the backsheet. Disposal tape 302 is used to hold a used (soiled) incontinence article in a rolled-up configuration after it has been torn along the seams 303 as shown in FIG. 5B. Although a variety of disposal tape constructions may be useful, in the illustrated embodiment, the disposal tape 302 includes two adjacent first and second tape tab elements 304, 306 separated by slit 336. Each of the first and second tape tab element 304, 306 is adhesively attached to a plastically deformable film 305, which is visible in FIG. 5B. More details about this disposal tape construction can be found in Int. Pat. Appl. Pub. No. WO 2007/032965 (Dahm et al.). In the illustrated embodiment, the tape tab elements 304, 306 each comprise a microporous film having an opaque, microporous region 322 and see-through regions of lower porosity 324 within the opaque, microporous region 322. The see-through regions of lower porosity 324 are in the form of alphabetical letters in the illustrated embodiment. However, as described above, the see-through regions can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired.

The personal hygiene article according to the present disclosure also includes sanitary napkins. A sanitary napkin typically includes a backsheet that is intended to be placed adjacent to the wearer's undergarment. Adhesive or mechanical fasteners are provided on the backsheet to attach the sanitary napkin to the wearer's undergarment. The sanitary napkin typically also includes a topsheet and absorbent core and may also include an acquisition layer. The backsheet, topsheet, acquisition layer, and absorbent core can be made from any of the materials described above for these components in diapers or incontinence articles. The sanitary napkin may have any desired shape such as an hourglass, keyhole, or generally rectangular shape. The topsheet and/or backsheet may also include flaps that are intended to wrap around to the opposite side of the wearer's undergarment. At least one of the topsheet, acquisition layer, flaps, or backsheet includes a microporous film having an opaque, microporous region and at least one see-through region of lower porosity within the opaque, microporous region. The see-through region of lower porosity or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, bar codes, or combination thereof may be part of a company name, logo, brand name, or trademark picture if desired.

Figure 2:
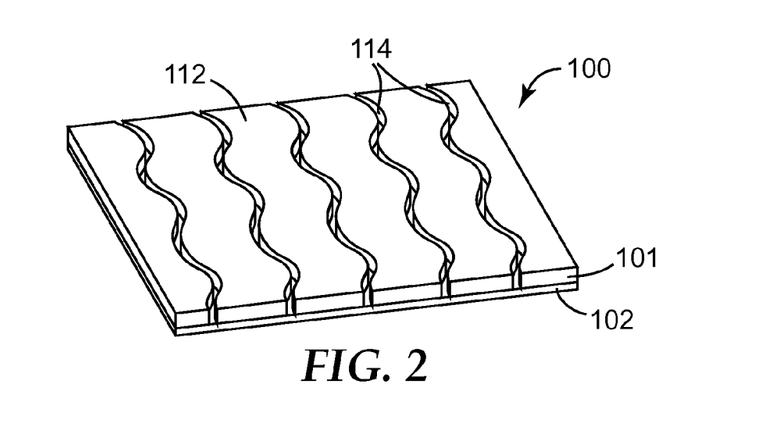
FIG. 2 is a perspective view of an embodiment of a laminate in which the microporous film useful in various embodiments of the present disclosure is a layer.

In some embodiments, the microporous film in the personal hygiene or container according to the present disclosure in any embodiment described herein is a first layer of a multilayer construction comprising the first layer and a second layer, and a portion of the second layer is visible through the at least one see-through region of lower porosity in the microporous film. FIG. 2 is a perspective view of a multilayer construction 100 in which the microporous film is a first layer 101. The microporous film has an opaque, microporous region 112 and a repeating series of see-through regions of lower porosity 114. The second layer 102 of the multilayer construction 100 is visible through the see-through regions 114. The microporous film may provide a portion of the personal hygiene article as described above, or the microporous film may provide a portion of a container as described below. The repeating series of see-through regions of lower porosity 114 may be made by a number of useful methods. For example, a nip made from two heated rolls in which one of the rolls has raised areas in the shape of the see-through regions 114 may be useful. The heat and pressure in the nip can collapse the microporous structure in the raised areas to form the see-through regions. The second layer 102 of the multilayer construction 100 may have a contrasting color that is visible between the see-through areas 114.

A multilayer construction such as that shown in FIG. 2 can be made in various ways, and the second layer 102 or other layers can be made from a variety of materials. In some embodiments, the second layer or other layers may comprise woven webs, non-woven webs (e.g., spunbond webs, spunlaced webs, airlaid webs, meltblown web, and bonded carded webs), textiles, plastic films (e.g., single- or multi-layered films, coextruded films, laterally laminated films, or films comprising foam layers), and combinations thereof. The second layer 102 or other layers may be colored (e.g., by inclusion of a pigment or dye). The second layer 102 or other layers may also be metalized. For any of these types of materials, the first and second layer can be joined by extrusion lamination, adhesives (e.g., pressure sensitive adhesives), or other bonding methods (e.g., ultrasonic bonding, compression bonding, or surface bonding). For example, in the case of plastic films, a first and second layer can be extruded separately and then laminated together. In some embodiments, the multilayer construction is a multilayer film made, for example, by coextrusion. A multilayer film of at least first and second layers can be coextruded using any suitable type of coextrusion die and any suitable method of film making such as blown film extrusion or cast film extrusion. In some embodiments, a multilayer melt stream can be formed by a multilayer feedblock, such as that shown in U.S. Pat. No. 4,839,131 (Cloeren). For the best performance in coextrusion, the polymeric compositions for each layer can be chosen to have similar properties such as melt viscosity. Techniques of coextrusion are found in many polymer processing references, including Progelhof, R. C., and Throne, J. L., "Polymer Engineering Principles", Hanser/Gardner Publications, Inc., Cincinnati, Ohio, 1993. In some embodiments, a first layer including a beta-nucleating agent or diluent as described below in a first polymeric composition can be coextruded with a second, different polymeric composition, lacking such an agent. The second polymeric composition may include a colorant such as a pigment or dye. Stretching the coextruded film can make the first layer opaque and microporous, effectively hiding the color in the second layer until the see-through region described herein is formed to reveal a portion of the second layer.

A multilayer film according to the present disclosure may have more than one microporous layer made by any of the methods described below. For example, a single second layer can have microporous layers on both of its surfaces. The single second layer may be colored. In other embodiments, multiple, different-colored layers may be interleaved with multiple microporous layers in an alternating fashion. In some embodiments, see-through regions of lower porosity are then made in certain of the microporous layers to reveal different colors in one or more see-through regions. These multilayer constructions can form the portion of the personal hygiene article or container according to the present disclosure.

Referring again to FIG. 2, in which the microporous film is a first layer 101 of a multilayer construction 100 comprising the first layer 101 and a second layer 102, and a portion of the second layer is visible through the at least one see-through region of lower porosity in the microporous film, the second layer 102 may be a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A similar process that also includes co-extruding a continuous outer skin layer on one or both outer faces of the side-by-side co-extruded film as described in U.S. Pat. No. 6,669,887 (Hilston et al.) may also be useful. Management of the flow of different polymer compositions into side-by-side lanes can also be carried out using a single manifold die with a distribution plate in contrast to approaches that require multiple dies to achieve side-by-side co-extrusion. Further details about the die and the distribution plate can be found, for example, in U.S. Pat. Appl. Pub. No. 2012/0308755 (Gorman et al.). Side-by-side co-extruded films can also be made by other extrusion dies that comprise a plurality of shims and have two cavities for molten polymer, such as those dies described, for example, in Int. Pat. App. Pub. No. WO 2011/119323 (Ausen et al.) and U.S. Pat. App. Pub. No. 2014/0093716 (Hanschen et al.). Extrusion dies for side-by-side co-extrusion are also available from Nordson Extrusion Dies Industries, Chippewa Falls, Wis. The side-by-side coextruded film may have different colors or different shades of the same color in different lanes so that more than one color can be seen through the see-through regions of lower porosity 114.

Figure 3:
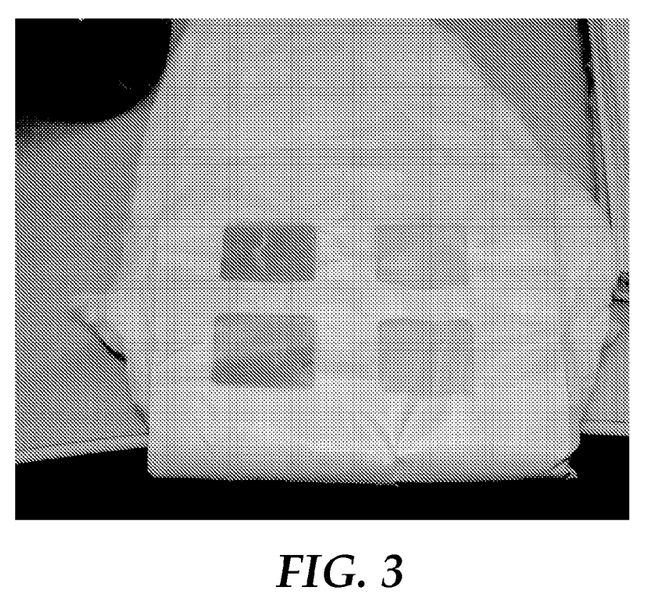
FIG. 3 is a photograph of an embodiment of a personal hygiene article the present disclosure.

A photograph of an embodiment of a personal hygiene article according to the present disclosure is shown in FIG. 3. In this embodiment, the microporous film has a see-through region made digitally with a laser. The microporous film may provide a portion of the backsheet as described above or a topsheet, or the microporous film may provide a portion of a container as described below.

Figure 4:
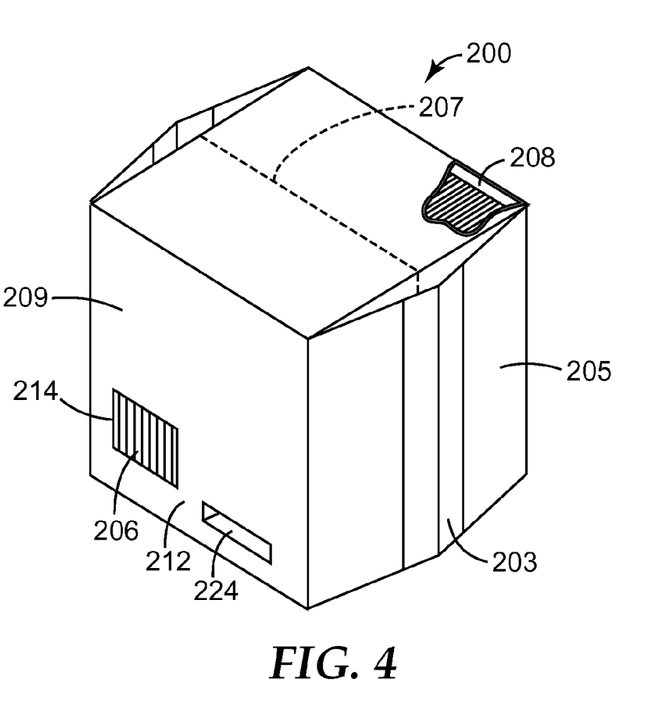
FIG. 4 is a perspective view of an embodiment of a container according to the present disclosure.

An embodiment of a container enclosing a plurality of personal hygiene articles is shown in FIG. 4. FIG. 4 illustrates a flexible container 200. Container 200 may be any useful shape, for example, the container 200 may have a polyhedral shape defining or forming a polyhedral enclosure. The interior 208 of the container 200 defines an interior space for containing personal hygiene articles 206. The personal hygiene articles 206 may be identical to one another or may be different from one another. In the illustrated embodiment, container 200 includes gussets 203 integrally formed with side faces 205 and a line of perforation 207 for accessing the personal hygiene articles 206. In other embodiments, the container can include tabs and adhesive openings or any other useful method for accessing the interior of the container. Container 200 includes a microporous film 209. The microporous film 209 has an opaque, microporous region 212 and at least one see-through region 214 of lower porosity forming a window within the opaque, microporous region 212. Similarly to the personal hygiene article shown in FIG. 1, microporous film 209 also includes a different see-through region of lower porosity 224 within the opaque, microporous region 212. The see-through region of lower porosity 214 or 224 or, in some embodiments, the pattern of see-through regions of lower porosity can be in the form of a number, picture, symbol, geometric shape, alphabetical letter, bar code, or any combination thereof. Any of these numbers, pictures, symbols, geometric shapes, alphabetical letters, or combination thereof may be part of a company name, logo, brand name, or trademark picture if desired. In some embodiments, the container according to the present disclosure may enclose only one personal hygiene article, for example, sanitary napkin.

Various methods are useful for making the microporous film disclosed herein. In some embodiments, the porosity in the microporous film, which may be a component of the personal hygiene article or the container in the various embodiments disclosed herein, results from beta-nucleation. Semi-crystalline polyolefins can have more than one kind of crystal structure. For example, isotactic polypropylene is known to crystallize into at least three different forms: alpha (monoclinic), beta (pseudohexangonal), and gamma (triclinic) forms. In melt-crystallized material the predominant form is the alpha or monoclinic form. The beta form generally occurs at levels of only a few percent unless certain heterogeneous nuclei are present or the crystallization has occurred in a temperature gradient or in the presence of shearing forces. The heterogeneous nuclei are typically known as beta-nucleating agents, which act as foreign bodies in a crystallizable polymer melt. When the polymer cools below its crystallization temperature (e.g., a temperature in a range from 60° C. to 120° C. or 90° C. to 120° C.), the loose coiled polymer chains orient themselves around the beta-nucleating agent to form beta-phase regions. The beta form of polypropylene is a meta-stable form, which can be converted to the more stable alpha form by thermal treatment and/or applying stress. Micropores can be formed in various amounts when the beta-form of polypropylene is stretched under certain conditions; see, e.g., Chu et al., "Microvoid formation process during the plastic deformation of β-form polypropylene", *Polymer*, Vol. 35, No. 16, pp. 3442-3448, 1994, and Chu et al., "Crystal transformation and micropore formation during uniaxial drawing of β-form polypropylene film", *Polymer*, Vol. 36, No. 13, pp. 2523-2530, 1995. Pore sizes achieved from this method can range from about 0.05 micrometer to about 1 micrometer, in some embodiments, about 0.1 micrometer to about 0.5 micrometer.

Generally, when the porosity in the microporous film is generated from a beta-nucleating agent, the film comprises a semi-crystalline polyolefin. Various polyolefins may be useful. Typically the semi-crystalline polyolefin comprises polypropylene. It should be understood that a semi-crystalline polyolefin comprising polypropylene may be a polypropylene homopolymer or a copolymer containing propylene repeating units. The copolymer may be a copolymer of propylene and at least one other olefin (e.g., ethylene or an alpha-olefin having from 4 to 12 or 4 to 8 carbon atoms). Copolymers of ethylene, propylene and/or butylene may be useful. In some embodiments, the copolymer contains up to 90, 80, 70, 60, or 50 percent by weight of polypropylene. In some embodiments, the copolymer contains up to 50, 40, 30, 20, or 10 percent by weight of at least one of polyethylene or an alpha-olefin. The semi-crystalline polyolefin may also be part of a blend of thermoplastic polymers that includes polypropylene. Suitable thermoplastic polymers include crystallizable polymers that are typically melt processable under conventional processing conditions. That is, on heating, they will typically soften and/or melt to permit processing in conventional equipment, such as an extruder, to form a sheet. Crystallizable polymers, upon cooling their melt under controlled conditions, spontaneously form geometrically regular and ordered chemical structures. Examples of suitable crystallizable thermoplastic polymers include addition polymers, such as polyolefins. Useful polyolefins include polymers of ethylene (e.g., high density polyethylene, low density polyethylene, or linear low density polyethylene), an alpha-olefin (e.g, 1-butene, 1-hexene, or 1-octene), styrene, and copolymers of two or more such olefins. The semi-crystalline polyolefin may comprise mixtures of stereo-isomers of such polymers, e.g., mixtures of isotactic polypropylene and atactic polypropylene or of isotactic polystyrene and atactic polystyrene. In some embodiments, the semi-crystalline polyolefin blend contains up to 90, 80, 70, 60, or 50 percent by weight of polypropylene. In some embodiments, the blend contains up to 50, 40, 30, 20, or 10 percent by weight of at least one of polyethylene or an alpha-olefin.

In some embodiments, the microporous film is made from a polymeric composition comprising a semi-crystalline polyolefin and having a melt flow rate in a range from 0.1 to 10 decigrams per minute, for example, 0.25 to 2.5 decigrams per minute.

When the porosity in the microporous film is generated from a beta-nucleating agent, the beta-nucleating agent may be any inorganic or organic nucleating agent that can produce beta-spherulites in a melt-formed sheet comprising polyolefin. Useful beta-nucleating agents include gamma quinacridone, an aluminum salt of quinizarin sulphonic acid, dihydroquinoacridin-dione and quinacridin-tetrone, triphenenol ditriazine, calcium silicate, dicarboxylic acids (e.g., suberic, pimelic, ortho-phthalic, isophthalic, and terephthalic acid), sodium salts of these dicarboxylic acids, salts of these dicarboxylic acids and the metals of Group IIA of the periodic table (e.g., calcium, magnesium, or barium), delta-quinacridone, diamides of adipic or suberic acids, different types of indigosol and cibantine organic pigments, quiancridone quinone, N',N'-dicyclohexil-2,6-naphthalene dicarboxamide (available, for example, under the trade designation "NJ-Star NU-100" from New Japan Chemical Co. Ltd.), antraquinone red, and bis-azo yellow pigments. The properties of the extruded film are dependent on the selection of the beta nucleating agent and the concentration of the beta-nucleating agent. In some embodiments, the beta-nucleating agent is selected from the group consisting of gamma-quinacridone, a calcium salt of suberic acid, a calcium salt of pimelic acid and calcium and barium salts of polycarboxylic acids. In some embodiments, the beta-nucleating agent is quinacridone colorant Permanent Red E3B, which is also referred to as Q-dye. In some embodiments, the beta-nucleating agent is formed by mixing an organic dicarboxylic acid (e.g., pimelic acid, azelaic acid, o-phthalic acid, terephthalic acid, and isophthalic acid) and an oxide, hydroxide, or acid salt of a Group II metal (e.g., magnesium, calcium, strontium, and barium). So-called two component initiators include calcium carbonate combined with any of the organic dicarboxylic acids listed above and calcium stearate combined with pimelic acid. In some embodiments, the beta-nucleating agent is aromatic tri-carboxamide as described in U.S. Pat. No. 7,423,088 (Mäder et al.).

The beta-nucleating agent serves the important functions of inducing crystallization of the polymer from the molten state and enhancing the initiation of polymer crystallization sites so as to speed up the crystallization of the polymer. Thus, the nucleating agent may be a solid at the crystallization temperature of the polymer. Because the nucleating agent increases the rate of crystallization of the polymer, the size of the resultant polymer particles, or spherulites, is reduced.

A convenient way of incorporating beta-nucleating agents into a semi-crystalline polyolefin useful for making a microporous film disclosed herein is through the use of a concentrate. A concentrate is typically a highly loaded, pelletized polypropylene resin containing a higher concentration of nucleating agent than is desired in the final microporous film. The nucleating agent is present in the concentration in a range of 0.01% to 2.0% by weight (100 to 20,000 ppm), in some embodiments in a range of 0.02% to 1% by weight (200 to 10,000 ppm). Typical concentrates are blended with non-nucleated polyolefin in the range of 0.5% to 50% (in some embodiments, in the range of 1% to 10%) by weight of the total polyolefin content of the microporous film. The concentration range of the beta-nucleating agent in the final microporous film may be 0.0001% to 1% by weight (1 ppm to 10,000 ppm), in some embodiments, 0.0002% to 0.1% by weight (2 ppm to 1000 ppm). A concentrate can also contain other additives such as stabilizers, pigments, and processing agents.

The level of beta-spherulites in the semi-crystalline polyolefin can be determined, for example, using X-ray crystallography and Differential Scanning calorimetry (DSC). By DSC, melting points and heats of fusion of both the alpha phase and the beta phase can be determined in a microporous film useful for practicing the present disclosure. For semi-crystalline polypropylene, the melting point of the beta phase is lower than the melting point of the alpha phase (e.g., by about 10 to 15 degrees Celsius). The ratio of the heat of fusion of the beta phase to the total heat of fusion provides a percentage of the beta-spherulites in a sample. The level of beta-spherulites can be at least 10, 20, 25, 30, 40, or 50 percent, based on the total amount of alpha and beta phase crystals in the film. These levels of beta-spherulites may be found in the film before it is stretched.

In some embodiments, the microporous film useful for practicing the present disclosure in any of its embodiments is formed using a thermally induced phase separation (TIPS) method. This method of making the microporous film typically includes melt blending a crystallizable polymer and a diluent to form a melt mixture. The melt mixture is then formed into a film and cooled to a temperature at which the polymer crystallizes, and phase separation occurs between the polymer and diluent, forming voids. In this manner a film is formed that comprises an aggregate of a plurality of crystallized polymer in the diluent compound. The voided film has some degree of opacity.

In some embodiments, following formation of the crystallized polymer, the porosity of the material is increased by at least one of stretching the film in at least one direction or removing at least some of the diluent. This step results in a network of interconnected micropores. This step also permanently attenuates the polymer to form fibrils, imparting strength and porosity to the film. The diluent can be removed from the material either before or after stretching. In some embodiments, the diluent is not removed. Pore sizes achieved from this method can range from about 0.2 micron to about 5 microns.

When the microporous film useful for practicing the present disclosure is made from a TIPS process, including embodiments in which the microporous film forms a portion of a component of the personal hygiene article or the container according to the present disclosure, the film can comprise any of the semi-crystalline polyolefins described above in connection with films made by beta-nucleation. In addition, other crystallizable polymers that may be useful alone or in combination include high and low density polyethylene, poly(vinylidine fluoride), poly(methyl pentene) (e.g., poly(4-methylpentene), poly(lactic acid), poly (hydroxybutyrate), poly(ethylene-chlorotrifluoroethylene), poly(vinyl fluoride), polyvinyl chloride, poly(ethylene terephthalate), poly(butylene terephthalate), ethylene-vinyl alcohol copolymers, ethylene-vinyl acetate copolymers, polybuyltene, polyurethanes, and polyamides (e.g., nylon-6 or nylon-66). Useful diluents for providing the microporous film according to the present disclosure include mineral oil, mineral spirits, dioctylphthalate, liquid paraffins, paraffin wax, glycerin, petroleum jelly, polyethylene oxide, polypropylene oxide, polytetramethylene oxide, soft carbowax, and combinations thereof. The quantity of diluent is typically in a range from about 20 parts to 70 parts, 30 parts to 70 parts, or 50 parts to 65 parts by weight, based upon the total weight of the polymer and diluent.

Particulate cavitating agents are also useful for making microporous films. Such cavitating agents are incompatible or immiscible with the polymeric matrix material and form a dispersed phase within the polymeric core matrix material before extrusion and orientation of the film. When such a polymer substrate is subjected to uniaxial or biaxial stretching, a void or cavity forms around the distributed, dispersed-phase moieties, providing a film having a matrix filled with numerous cavities that provide an opaque appearance due to the scattering of light within the matrix and cavities. The microporous film can comprise any of the polymers described above in connection with TIPS films. The particulate cavitating agents may be inorganic or organic. Organic cavitating agents generally have a melting point that is higher than the melting point of the film matrix material. Useful organic cavitating agents include polyesters (e.g., polybutylene teraphthalate or nylon such as nylon-6), polycarbonate, acrylic resins, and ethylene norbornene copolymers. Useful inorganic cavitating agents include talc, calcium carbonate, titanium dioxide, barium sulfate, glass beads, glass bubbles (that is, hollow glass spheres), ceramic beads, ceramic bubbles, and metal particulates. The particle size of cavitating agents is such that at least a majority by weight of the particles comprise an overall mean particle diameter, for example, of from about 0.1 micron to about 5 microns, in some embodiments, from about 0.2 micron to about 2 microns. (The term "overall" refers to size in three dimensions; the term "mean" is the average.) The cavitating agent may be present in the polymer matrix in an amount of from about 2 weight percent to about 40 weight percent, about 4 weight percent to about 30 weight percent, or about 4 weight percent to about 20 weight percent, based upon the total weight of the polymer and cavitating agent. In some embodiments, microporous films made from cavitating agents may have at least one of lower opacity in a microporous region or higher opacity in a region in which the pores are collapsed than a microporous film made from a beta-nucleating agent.

Additional ingredients may be included in the microporous film useful for practicing any of the embodiments of the present disclosure, depending on the desired application. For example, surfactants, antistatic agents, ultraviolet radiation absorbers, antioxidants, organic or inorganic colorants, stabilizers, flame retardants, fragrances, nucleating agents other than a beta-nucleating agent, and plasticizers may be included. Many of the beta-nucleating agents described above have a color. Also, colorants may be added, for example, in the form of a color concentrate or a colored master batch.

For the microporous films made by any of the methods described above, the film is typically stretched to form or enhance the microporous structure. Stretching the film can be carried out on a web biaxially or monoaxially. Biaxial stretching means stretching in two different directions in the plane of the backing. Typically, but not always, one direction is the machine direction or longitudinal direction "L", and the other, different direction is the cross direction or width direction "W". Biaxial stretching can be performed sequentially by stretching the thermoplastic backing, for example, first in one of the longitudinal or width direction and subsequently in the other of the longitudinal or width direction. Biaxial stretching can also be performed essentially simultaneously in both directions. Monoaxial stretching refers to stretching in only one direction in the plane of the backing. Typically, monoaxial stretching is performed in one of the "L" or "W" direction but other stretch directions are also possible.

In some embodiments, the stretching increases at least one of the film's length ("L") or width ("W") at least 1.2 times (in some embodiments, at least 1.5, 2, or 2.5 times). In some embodiments, the stretching increases both of the film's length ("L") and width ("W") at least 1.2 times (in some embodiments, at least 1.5, 2, or 2.5 times). In some embodiments, the stretching increases at least one of the film's length ("L") or width ("W") up to 5 times (in some embodiments, up to 2.5 times). In some embodiments, the stretching increases both of the film's length ("L") and width ("W") up to 5 times (in some embodiments, up to 2.5 times). In some embodiments, the stretching increases at least one of the film's length ("L") or width ("W") up to 10 times (in some embodiments, up to 20 times or more). In some embodiments, the stretching increases both of the film's length ("L") and width ("W") up to 10 times (in some embodiments, up to 20 times or more).

In general, when a thermoplastic film is monoaxially or biaxially stretched at a temperature below the melting point of the thermoplastic material, particularly at a temperature below the line drawing temperature of the film, the thermoplastic film may stretch non-uniformly, and a clear boundary is formed between stretched and unstretched parts. This phenomenon is referred to as necking or line drawing. However, substantially the entire thermoplastic backing is stretched uniformly when it is stretched to a sufficiently high degree. The stretch ratio at which this occurs is referred to as the "natural stretch ratio" or "natural draw ratio." Stretching above the natural stretch ratio is understood to provide significantly more uniform properties or characteristics such as thickness, tensile strength, and modulus of elasticity. For any given thermoplastic backing and stretch conditions, the natural stretch ratio is determined by factors such as the composition of the thermoplastic resin forming the thermoplastic backing, the morphology of the formed thermoplastic backing due to quenching conditions on the tool roll, for example, and temperature and rate of stretching. Furthermore, for biaxially stretched thermoplastic backings, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in the first direction and one in the second direction) which result in the natural stretch ratio. The term "stretch ratio" refers to ratio of a linear dimension of a given portion of the thermoplastic backing after stretching to the linear dimension of the same portion before stretching. The natural stretch ratio of the most common crystalline form of polypropylene, the alpha form, has been reported to be about 6:1.

Stretching the film useful for practicing the present disclosure can be carried out in a variety of ways. When the film is a web of indefinite length, for example, monoaxial stretching in the machine direction can be performed by propelling the film over rolls of increasing speed. The term "machine direction" (MD) as used herein denotes the direction of a running, continuous web of the film. A versatile stretching method that allows for monoaxial, sequential biaxial, and simultaneous biaxial stretching of the film employs a flat film tenter apparatus. Such an apparatus grasps the thermoplastic web using a plurality of clips, grippers, or other film edge-grasping means along opposing edges of the film in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. The term "cross-direction" (CD) as used herein denotes the direction which is essentially perpendicular to the machine direction. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany.

Stretching the film is typically performed at elevated temperatures, for example, up to 150° C. Heating the film may allow it to be more flexible for stretching. Heating can be provided, for example, by IR irradiation, hot air treatment or by performing the stretching in a heat chamber. In some embodiments, stretching the film is carried out at a temperature range from 50° C. to 130° C.

In the personal hygiene article and container according to the present disclosure, the film may have a variety of thicknesses. For example, the initial thickness (i.e., before any stretching) of the film may be up to about 750, 500, 400, 250, or 150 micrometers, depending on the desired application. In some embodiments, the initial thickness of the film is at least about 50, 75, or 100 micrometers, depending on the desired application. In some embodiments, the initial thickness of the film is in a range from 50 to about 225 micrometers, from about 75 to about 200 micrometers, or from about 100 to about 150 micrometers. The film may have an essentially uniform cross-section, or the film may have structure, which may be imparted, for example, by at least one forming roll.

In some embodiments, stretching a film described above in order to form or enhance microporosity provides an increase in opacity of at least 10, 15, 20, 25, or 30 percent. The increase in opacity may be, for example, up to 90, 85, 80, 75, 70, 65, 60, 55, or 50 percent. The initial opacity is affected, for example, by the thickness of the film. Stretching a film typically results in a decrease in thickness, which would typically lead to a decrease in opacity. However, stress whitening and micropore formation leads to an increase in opacity. For the purposes of the present disclosure, opacity can be measured using a spectrophotometer with the "L" value measured separately against a black background and against a white background, respectively. The opacity is calculated as (L measured against the black background/L measured against the white background) times 100. The "L" value is one of three standard parameters in the CIELAB color space scale established by the International Commission on Illumination. "L" is a brightness value, ranging from 0 (black) to 100 (highest intensity). A percentage change in opacity that results from stretching is calculated by [(opacity after stretching−opacity before stretching)/opacity before stretching]times 100.

In some embodiments, stretching a film described above in order to form or enhance microporosity provides a decrease in the grayscale value of the film of at least twenty percent. In some embodiments, stretching provides a decrease in a grayscale value of at least 25, 30, 40, or 50 percent. The decrease in grayscale value may be, for example, up to 90, 85, 80, 75, 70, 65, or 60 percent. For the purposes of this disclosure, the grayscale value is measured in transmission mode using the method described in the Example section, below. Stretching a film typically results in a decrease in thickness, which would typically lead to an increase in the grayscale value measured in transmission mode. However, stress whitening and micropore formation leads to decrease in transmission mode grayscale values. A percentage change in grayscale value that results from stretching the film is calculated by [(grayscale value after stretching−grayscale value before stretching)/grayscale value before stretching]times 100. In some embodiments, the microporous film has a grayscale value of up to 40 (in some embodiments, up to 35, 30, 25, 20 or 15). In some embodiments, the grayscale values for the microporous films disclosed herein are comparable or better than those achieved for polyolefin films of similar composition but incorporating conventional amounts of IR blocking agents such as titanium dioxide.

The opacity and grayscale measurement of the microporous film relate to its ability to transmit light. As used herein, the term "light" refers to electromagnetic radiation, whether visible to the unaided human eye or not. Ultraviolet light is light having a wavelength in a range from about 250 nanometers (nm) to 380 nm. Visible light is light having a wavelength in a range from 380 nanometers (nm) to 700 nm. Infrared light has a wavelength in a range from about 700 nm to 300 micrometers. After the microporous film useful for practicing the present disclosure has been stretched, it has decreased transmission to ultraviolet, visible, and infrared light. The micropores in the stretched film tend to scatter light in the ultraviolet, visible, and infrared ranges.

As described above, heat, pressure, or a combination thereof may be useful for providing the see-through regions. Typically, the at least one see-through region of lower porosity is heated to the melting temperature of the thermoplastic in the microporous film. Melting the microporous film in the at least one see-through region results in a permanent change in the structure of the film in the see-through region, which can be accompanied by some film shrinkage in that region. Heating can be carried out in a press or a heated nip having a raised image of the at least one see-through region so that pressure accompanies the heating to collapse the microporous structure. Pressure alone may provide a temporary change in the microporous structure of the microporous film in some instances. When using a static press, it can be useful to use a rubber surface on the film side opposite the side that is exposed to the raised and heated image. The rubber surface can prevent two hard surfaces from forming a hole in the film while the see-through region is being made. In a nip, the pressure and gap can be adjusted as well as the line speed to prevent forming holes in the film.

Heating may also be carried out with hot air or with a directed radiation source such as a laser. A variety of different types of laser may be useful. For example, a carbon dioxide laser may be useful. An ultraviolet laser and diode laser may also be useful. Suitable wavelengths for the laser can in a range from 200 nm to 11,000 nm. The laser wavelength and absorption properties of the material can be selected to be matched or nearly matched so as to create the heating of material. For a person skilled in the art, the suitable power for the laser, beam size on the material, and speed of the beam movement across the material can be adjusted to achieve the desired heating. This matching of laser and material can be advantageous, for example, when the microporous film is a layer with a multilayer construction. Heating with the laser can be adjusted to a location of the microporous film with the multilayer construction (e.g., multilayer film). The heating can be made in a pattern by directing the radiation across the surface to expose an area of material, or the radiation can be directed across the surface of a suitable mask so that a patterned area is exposed to the radiation. The microporous film may be positioned outside of the focal plane of the laser to adjust the level of heating.

For some applications such as heat seal films, recording media, and oil-absorbing cosmetic sheets, it has been shown that changing the microporous structure in a region of a microporous film can change the opacity in that region. See, for example, GB 2323327, published Sep. 23, 1998, GB 2252838, published Aug. 19, 1992, and U.S. Pat. App. Pub. No. 2003/091618 (Seth et al.). However, in some of these cases, the change is provided in a random fashion, for example, by an impact during the use of the film that cannot provide a predetermined pattern or image. A change in the microporous structure by impact may also not be permanent. In other cases, the change is only provided along the edge of a film and therefore does not provide at least one see-through region within an opaque, microporous region.

Referring again to FIG. 1, target area 68 may include a microporous film described herein. Examples of loop tapes that may suitably be applied to the target area 68 to provide an exposed fibrous material 72, are disclosed, for example, in U.S. Pat. No. 5,389,416 (Mody et al.) and U.S. Pat. No. 5,256,231 (Gorman et al.) and EP 0,341,993 (Gorman et al.). As described in U.S. Pat. No. 5,256,231 (Gorman et al.), the fibrous layer in a loop material according to some embodiments can comprise arcuate portions projecting in the same direction from spaced anchor portions on a film. Any of the fibrous loop materials may be extrusion-bonded, adhesive-bonded, and/or sonically-bonded to the microporous film described herein. For loop materials extrusion bonded to the microporous film, stretching the film to provide or enhance porosity is typically carried out after the extrusion bonding. Stretching the microporous film may be carried out before or after adhesively or sonically bonding the fibrous loop material to the microporous film. The microporous film bonded to the fibrous loop material can be useful as a target area (or landing zone) in the personal hygiene article according to the present disclosure.

The microporous regions in the personal hygiene articles and containers according to the present disclosure provide advantages other than the contrast between the microporous region and the at least one see-through region. The ability of the microporous films to block the transmission of light (e.g., by scattering) allows them to be detected in inspection systems that rely upon shining a light onto a substrate and detecting the amount of light received from the area of the irradiated substrate. For example, in the manufacture of a personal hygiene article, the presence or position of a microporous film disclosed herein or a portion thereof incorporated into the article can be detected because of its ability to block ultraviolet, visible, and/or infrared light. The response of the microporous film to irradiation by at least one of ultraviolet, visible, or infrared light is evaluated. Subsequently, during manufacturing a personal hygiene article can be irradiated, and at least one of the ultraviolet, visible, or infrared radiation received from the irradiated personal hygiene article can be detected and analyzed for the predefined response of the microporous film. The position of the microporous film can be determined using an image analyzer that can detect predefined variations in grayscale values, for example, that correspond to the positions of the microporous film and other components. The ability of the microporous film disclosed herein to scatter infrared light allows it to be detected even when it is between other layers of materials in the composite article. For more information regarding methods of detecting microporous films in a composite article, see U.S. Pat. App. Pub. No. 2013/0147076 (Chandrasekaran et al.).

Furthermore, microporous films tend to have lower densities than their non-microporous counterparts. A low-density microporous film feels softer to the touch than films having comparable thicknesses but higher densities. The density of the film can be measured using conventional methods, for example, using helium in a pycnometer. In some embodiments, stretching a film containing beta-spherulites provides a decrease in density of at least three percent. In some embodiments, this stretching provides at decrease in density of at least 5 or 7.5 percent. For example, the stretching provides at decrease in density in a range from 3 to 15 percent or 5 to 10 percent. A percentage change in density that results from stretching the film is calculated by [(density before stretching−density after stretching)/density before stretching]times 100. The softness of the film can be measured, for example, using Gurley stiffness.

As described above in connection with FIG. 2, the microporous film may be a first layer of a laminate comprising the first layer and a second layer, and a portion of the second layer is visible through the at least one see-through region of lower porosity. It is also possible for the microporous film useful for practicing the present disclosure to be a side-by-side co-extruded film. Side-by-side co-extruded films can be made by a number of useful methods. For example, U.S. Pat. No. 4,435,141 (Weisner et al.) describes a die with die bars for making a multi-component film having alternating segments in the film cross-direction. A similar process that also includes co-extruding a continuous outer skin layer on one or both outer faces of the side-by-side co-extruded film as described in U.S. Pat. No. 6,669,887 (Hilston et al.) may also be useful. Management of the flow of different polymer compositions into side-by-side lanes can also be carried out using a single manifold die with a distribution plate in contrast to approaches that require multiple dies to achieve side-by-side co-extrusion. Further details about the die and the distribution plate can be found, for example, in U.S. Pat. Appl. Pub. No. 2012/0308755 (Gorman et al.). Side-by-side co-extruded films can also be made by other extrusion dies that comprise a plurality of shims and have two cavities for molten polymer, such as those dies described, for example, in Int. Pat. App. Pub. No. WO 2011/119323 (Ausen et al.) and U.S. Pat. App. Pub. No. 2014/0093716 (Hanschen et al.). Extrusion dies for side-by-side co-extrusion are also available from Nordson Extrusion Dies Industries, Chippewa Falls, Wis.

In some embodiments, the microporous film useful for practicing the present disclosure is a coextruded film having side-by-side first and second lanes, wherein the first lanes comprise the opaque, microporous region and at least one see-through region of lower porosity within the opaque, microporous region, and wherein the second lanes comprise a different polymer composition, which may not be microporous. In some embodiments, the microporous film is a multilayer film having first and second layers, wherein the first layer comprises the opaque, microporous region and at least one see-through region of lower porosity within the opaque, microporous region, and wherein the second layer comprises a different polymer composition, which may not be microporous. Suitable thermoplastic materials for the different polymer composition include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. In some embodiments, the different polymer composition (e.g., in the second lanes or second layer) includes an alpha nucleating agent (e.g., in polypropylene). In some embodiments, the different polymer composition includes a colorant such as a pigment or dye.

One or more zones of the personal hygiene article or container may comprise one or more elastically extensible materials extending in at least one direction when a force is applied and returning to approximately their original dimension after the force is removed. The term "elastic" refers to any material that exhibits recovery from stretching or deformation. Likewise, "nonelastic" materials, which do not exhibit recovery from stretching or deformation, may be useful for the personal hygiene article or container as well.

In some embodiments, the different polymer composition in the second lanes or second layer of a multilayer or side-by-side coextruded film includes an elastomeric material. The term "elastomeric" refers to polymers from which films (0.002 to 0.5 mm thick) can be made that exhibit recovery from stretching or deformation. Examples of elastomeric polymeric compositions which can be used in the segmented multicomponent polymeric films disclosed herein include thermoplastic elastomers such as ABA block copolymers, polyurethane elastomers, polyolefin elastomers (e.g., metallocene polyolefin elastomers), polyamide elastomers, ethylene vinyl acetate elastomers, and polyester elastomers. An ABA block copolymer elastomer generally is one where the A blocks are polystyrenic, and the B blocks are conjugated dienes (e.g., lower alkylene dienes). The A block is generally formed predominantly of substituted (e.g, alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, for example, in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastomers can be blended with block copolymer elastomers provided that the elastomeric properties are not adversely affected. Many types of thermoplastic elastomers are commercially available, including those from BASF under the trade designation "STYROFLEX", from Shell Chemicals under the trade designation "KRATON", from Dow Chemical under the trade designation "PELLETHANE" or "ENGAGE", from DSM under the trade designation "ARNITEL", from DuPont under the trade designation "HYTREL", and more. The thermoplastic elastomers including tetrablock styrene/ethylene-propylene/styrene/ethylene-propylene described in U.S. Pat. No. 6,669,887 (Hilston et al.) may also be useful.

Some Embodiments of the Disclosure

In a first embodiment, the present disclosure provides a personal hygiene article comprising a chassis with a topsheet, a backsheet, and an absorbent component between the topsheet and the backsheet, wherein at least one portion of the personal hygiene article comprises a microporous film having an opaque, microporous region and at least one see-through region of lower porosity within the opaque, microporous region, and wherein the microporous film comprises a beta-nucleating agent or has thermally induced phase separation caused by a diluent.

In a second embodiment, the present disclosure provides the personal hygiene article of the first embodiment, wherein the personal hygiene article is a diaper or incontinence article.

In a third embodiment, the present disclosure provides the personal hygiene article of the first embodiment, wherein the personal hygiene article is a sanitary napkin.

In a fourth embodiment, the present disclosure provides the personal hygiene article of any one of the first to third embodiments, wherein the at least one portion of the personal hygiene article is a laminate of a first layer comprising the microporous film and a second layer, and wherein a portion of the second layer is visible through the at least one see-through region of lower porosity.

In a fifth embodiment, the present disclosure provides the personal hygiene article of the fourth embodiment, wherein the first layer and second layer have different colors or different shades of the same color.

In a sixth embodiment, the present disclosure provides the personal hygiene article of any one of the first to fifth embodiments, wherein the topsheet comprises the microporous film having an opaque, microporous region and at least one see-through region of lower porosity within the opaque, microporous region.

In a seventh embodiment, the present disclosure provides the personal hygiene article of any one of the first to sixth embodiments, wherein the backsheet comprises the microporous film having an opaque, microporous region and at least one see-through region of lower porosity within the opaque, microporous region.

In an eighth embodiment, the present disclosure provides the personal hygiene article of any one of the first to seventh embodiments, wherein an acquisition layer between the topsheet and the backsheet comprises the microporous film having an opaque, microporous region and at least one see-through region of lower porosity within the opaque, microporous region.

In a ninth embodiment, the present disclosure provides the personal hygiene article of any one of the first to eighth embodiments, wherein the personal hygiene article further comprises first and second opposing longitudinal edges extending from a rear waist region to an opposing front waist region, and wherein a side panel attached along at least a portion of the first or second longitudinal edge comprises the microporous film having an opaque, microporous region and at least one see-through region of lower porosity within the opaque, microporous region.

In a tenth embodiment, the present disclosure provides the personal hygiene article of any one of the first to ninth embodiments, wherein the personal hygiene article further comprises first and second opposing longitudinal edges extending from a rear waist region to an opposing front waist region, and wherein an ear attached along at least a portion of the first or second longitudinal edge comprises the microporous film having an opaque, microporous region and at least one see-through region of lower porosity within the opaque, microporous region.

In an eleventh embodiment, the present disclosure provides the personal hygiene article of any one of the first to tenth embodiments, wherein at least one of a loop tape or a disposal tape on the backsheet comprises the microporous film having an opaque, microporous region and at least one see-through region of lower porosity within the opaque, microporous region.

In a twelfth embodiment, the present disclosure provides a container comprising a microporous film enclosing at least one personal hygiene article, the microporous film having an opaque, microporous region and at least one see-through region of lower porosity forming a window within the opaque, microporous region.

In a thirteenth embodiment, the present disclosure provides the container of the twelfth embodiment, wherein each personal hygiene article comprises a chassis with a topsheet, a backsheet, an absorbent component between the topsheet and the backsheet.

In a fourteenth embodiment, the present disclosure provides the container of the twelfth or thirteenth embodiment, wherein each personal hygiene article is a diaper or incontinence article.

In a fifteenth embodiment, the present disclosure provides the container of the twelfth or thirteenth embodiment, wherein each personal hygiene article is a sanitary napkin.

In a sixteenth embodiment, the present disclosure provides the personal hygiene article or container of any one of the first to fifteenth embodiments, wherein the at least one see-through region of lower porosity is included in a pattern of see-through regions of lower porosity within the opaque, microporous region.

In a seventeenth embodiment, the present disclosure provides the personal hygiene article or container of any one of the first to sixteenth embodiments, wherein the at least one see-through region of lower porosity is in the form of a number, symbol, picture, geometric shape, alphabetical letter, or combination thereof.

In an eighteenth embodiment, the present disclosure provides the personal hygiene article or container of any one of the first to seventeenth embodiments, wherein the microporous film comprises a beta-nucleating agent.

In a nineteenth embodiment, the present disclosure provides the personal hygiene article or container of any one of the first to seventeenth embodiments, wherein the microporous film has thermally induced phase separation caused by a diluent.

In a twentieth embodiment, the present disclosure provides the personal hygiene article or container of any one of the first to nineteenth embodiments, wherein the microporous film comprises at least one of propylene homopolymer, a copolymer of propylene and other olefins, or a blend of a polypropylene homopolymer and a different polyolefin.

In a twenty-first embodiment, the present disclosure provides a method of making the personal hygiene article or the container of any one of the first to twentieth embodiments, the method comprising:

providing a microporous film;

collapsing some pores in the microporous film to form the at least one see-through region of lower porosity within the opaque, microporous region of the microporous film; and assembling at least a portion of the microporous film including the at least one see-through region of lower porosity and the opaque, microporous region into the personal hygiene article or into the container.

In a twenty-second embodiment, the present disclosure provides a method of making the personal hygiene article of any one of the first to eleventh embodiments or any one of the sixteenth to twentieth embodiments as dependent on any one of the first to eleventh embodiments, the method comprising:

providing a microporous film;

collapsing some pores in the microporous film to form at least one see-through region of lower porosity within an opaque, microporous region of the microporous film; and assembling at least a portion of the microporous film including the at least one see-through region of lower porosity and the opaque, microporous region into the personal hygiene article.

In a twenty-third embodiment, the present disclosure provides a method of making the container of any one of the twelfth to fifteenth embodiments or any one of the sixteenth to twentieth embodiments as dependent on any one of the twelfth to fifteenth embodiments, the method comprising:

providing a microporous film;

collapsing some pores in the microporous film to form the at least one see-through region of lower porosity within the opaque, microporous region of the microporous film; and assembling the microporous film into the container enclosing the at least one personal hygiene article.

In a twenty-fourth embodiment, the present disclosure provides the method of any one of the twenty-first to twenty-third embodiments, wherein collapsing some pores in the microporous film comprises heating the microporous film to collapse the pores to form the at least one see-through region of lower porosity.

In a twenty-fifth embodiment, the present disclosure provides the method of the twenty-fourth embodiment, wherein heating the microporous film is carried out with a heated, patterned roller.

In a twenty-sixth embodiment, the present disclosure provides the method of the twenty-fourth embodiment, wherein heating the microporous film is carried out with hot air.

In a twenty-seventh embodiment, the present disclosure provides the method of the twenty-fourth embodiment, wherein heating the microporous film is carried out with a laser.

In a twenty-eighth embodiment, the present disclosure provides the method of the twenty-seventh embodiment, wherein the microporous film is a layer in a multilayer film, and wherein the heating with the laser is adjusted to a location of the microporous film within the multilayer film.

In a twenty-ninth embodiment, the present disclosure provides the method of any one of the twenty-first to twenty-eighth embodiments, wherein providing the microporous film comprises stretching a film comprising at least one of a beta-nucleating agent or a diluent.

In a thirtieth embodiment, the present disclosure provides the method of any one of the twenty-first to twenty-ninth embodiments, wherein providing the microporous film comprises melt blending a crystallizable polymer and a diluent and cooling to a temperature at which the polymer crystallizes and phase separates from the diluent.

In order that this disclosure can be more fully understood, the following examples are set forth. It should be understood that these examples are for illustrative purposes only and are not to be construed as limiting this disclosure in any manner.

EXAMPLES

Example 1

A film was prepared by feeding a stream of a polypropylene impact copolymer, obtained from the Dow Chemical Company, Midland, Mich., under the trade designation "DOW C700-35N POLYPROPYLENE RESIN" (98 weight %) and a beta nucleating master batch obtained from the Mayzo Corporation, Alpharetta, Ga., under the trade designation "MPM 1114" (2 weight %) through a 2 inch (5.08 cm) single screw extruder. The polymer density was reported by the manufacturer to be 0.902 g/cc as measured according to ASTM D972, and the melt flow index (MFI) was reported to be 35 (at 230° C. and under the load of 2.16 kg) as measured according to ASTM D1238. The beta nucleating master batch was pelletized and contained a high performance beta nucleant formulation dispersed in a polypropylene homopolymer resin. Seven barrel zones in the extruder were set at 176° C., 170° C., 180° C., 190° C., 200° C., 218° C., and 218° C., respectively. The molten resin was then fed through a sheet die to a smooth chrome roll. The temperature of the die was set at 218° C. and the temperature of the roll was set at 90° C. The screw speed was set at 80 rpm. The chrome roll was water-cooled to provide rapid quenching that maintained the orientation in the polymer. The line speed was set such that the film thickness was 100 micrometers. The film was then stretched in the machine direction by passing the web through two sets of rolls in which one roll was rotating faster than the other one. For each set of rolls, the bottom roll was a chrome roll, and the top roll was a rubber roll. For stretching, the temperature of each bottom chrome roll was set at 71° C. (160° F.) and that of each top rubber roll was set at 71° C. (160° F.). The draw ratio was 2:1 in the machine direction.

A sample of the film was exposed to laser radiation at 10.6 micron wavelength from a $CO_2$ laser, E-400 from Coherent, Inc., Santa Clara, Calif. The laser energy was directed across the sample by a scanner Model HPLK 1330 from GSI Group, Billerica, Mass. The sample was positioned at a distance of approximately 510 mm from the scanner housing (whereas the focal plane of the scanner system was located at approximately 560 mm from the scanner housing). In the plane of the sample, the spot size for the laser beam was determined to be approximately 0.9 mm in width with a nearly circular shape. To provide a patterned exposure, the laser beam was scanned in a raster motion to create a filled shape of a rectangle, dimensions 2.5 cm by 2 cm. Four of such rectangles were made. The laser beam with a power of approximately 25 Watts was scanned at a speed of approximately 930 mm/sec in a raster motion across the mask with successive lines separated by approximately 0.5 mm. The laser radiation was incident upon the sample material and affected the change in appearance.

The backsheet consisting of a non-woven material was removed from a diaper by spraying compressed air to detackify the adhesive. The square patterned film was then cut into a sheet 20 cm by 12 cm, and colored sheets were attached underneath with a double sided tape. The sandwich was then attached to the top of the diaper which is shown in FIG. 3. The colored sheets could be readily seen through the rectangles.

Example 2

A formed sheet of 9 denier polypropylene fibers was prepared according to the method of Example Number 1 of U.S. Pat. No. 5,256,231 (Gorman et al.) Polypropylene obtained from the Dow Chemical Company under the trade designation "DOW C700-35N POLYPROPYLENE RESIN" (98 weight %) and the beta nucleating master batch obtained from the Mayzo Corporation under the trade designation "MPM 1114" (2 weight %) were extruded through a die at a die temperature of 420° F. (216° C.) and onto the anchor portions of the formed sheet of fibers just before the nip between the first corrugating roller and a cooling roller in an amount appropriate to form the thermoplastic backing layer and cause it to be about 0.0381 centimeter thick with the anchor portions of the formed sheet of fibers embedded therein, whereupon the formed sheet of fibers and the thermoplastic backing layer moved through the nip between the first corrugating roller and the cooling roller and about 200 degrees around the periphery of the cooling roller, which was at a temperature of about 85° F. to ensure adequate cooling of the thermoplastic backing layer. The laminate was then stretched in the machine direction by passing the web through two sets of rolls in which one roll was rotating faster that the other one. For each set of rolls, the bottom roll was a chrome roll, and the top roll was a rubber roll. For stretching, the temperature of each bottom chrome roll was set at 71° C. (160° F.) and that of each top rubber roll was set at 71° C. (160° F.). The draw ratio was 1.4:1 in the machine direction.

The laminate was then passed through a heated nip consisting of one patterned roll at the bottom and a polished chrome roll on top. The pattern roll had the pattern shown in FIG. 2. The surface temperature of the patterned roll was set to 140° C. with a nip pressure of 1000 N. The nip gap was set to 0.005 cm. The laminate in the patterned areas was see-through so that colored sheets placed behind the laminate could easily be seen.

The laminate could be useful, for example, as at least a portion of a backsheet (e.g., a target area on the backsheet).

Example 3

The poly(vinylidene fluoride) (PVDF) polymer pellets obtained from Solvay Solexis, Thorofare, N.J., under trade name "SOLEF 1012" were introduced into the hopper of a 25 mm co-rotating twin-screw extruder with an approximate total extrusion rate of 3.6-4.5 kilograms per hour and a screw speed of 150 RPM. The nucleating agent CHROMOPHTAL Blue A3R (Ciba Specialty Chemicals, Hawthorne, N.Y.) in powder form, was premixed with the glyceryl triacetate diluent obtained from (Eastman Kodak Co., Rochester, N.Y.) in a Mini-Zeta bead mill and then fed, with additional diluent by a feeding device into the extruder via a port in the extruder wall intermediate the hopper and the extruder exit. The polymer to diluent ratio was varied slightly in accordance with the amount of nucleator used, but was generally approximately 0.41:1.0. The extruder had eight zones with a temperature profile of zone 1 at 204° C., zone 2 at 266° C., zone 3 at 266° C., zone 4 at 221° C., zone 5 at 182° C., zone 6 at 182° C., zone 7 at 182° C. The melt was subsequently pumped through a double-chromed coat-hanger slot film die, cast onto a chrome roll that ranged from 52° C. and then wound into a roll. Film samples were cut from the rolls and placed in metal frames measuring 15 cm by 28 cm. The frames were then placed in small pans of deionized water for 20 minutes (effectively removing the TRIACETIN diluent from the films) and then allowed to dry in ambient air. The washed film samples were then stretched biaxially 1.75 by 1.75 on a TM Long Film Stretcher (TM Long Co., Somer- ville, N.J.) at 132° C. The films were held in the stretcher for 2-5 minutes at 132° C. after stretching was complete to anneal the film.

A 20 cm by 6 cm piece was cut from the film, and the sample was placed on a machined aluminum plate coated with 0.5 cm thick silicone rubber. The edges of the sample were fixed to the aluminum plate using adhesive tape. An aluminum plate that was engraved with a wave pattern was mounted to the top plate of a compression press which is movable by using compressed air. The top plate was heated to a surface temperature of 130° C. (266° F.). The sample was fixed to the bottom plate of the press, which is a fixed plate. The top plate was pressed against the bottom plate for 6 seconds in order to emboss the wave pattern on to the sample.

The film could be useful, for example, as a backsheet or as a microporous film for a container enclosing personal hygiene articles.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A personal hygiene article comprising a chassis with a topsheet, a backsheet, and an absorbent component between the topsheet and the backsheet, wherein at least one portion of the personal hygiene article comprises a microporous film having an opaque, microporous region and at least one see-through region of lower porosity within the opaque, microporous region, and wherein the microporous film comprises a beta-nucleating agent.

2. The personal hygiene article of claim 1, wherein the at least one see-through region of lower porosity is included in a pattern of see-through regions of lower porosity within the opaque, microporous region.

3. The personal hygiene article of claim 1, wherein the at least one see-through region of lower porosity is in the form of a number, symbol, picture, geometric shape, bar code, an alphabetical letter, or a combination thereof.

4. The personal hygiene article of claim 1, wherein the at least one portion of the personal hygiene article is a multi-layer construction of a first layer comprising the microporous film and a second layer, and wherein a portion of the second layer is visible through the at least one see-through region of lower porosity.

5. The personal hygiene article of claim 4, wherein the first layer and the second layer have different colors or different shades of the same color.

6. The personal hygiene article of claim 1, wherein at least one of the topsheet, the backsheet, an acquisition layer between the topsheet and the backsheet, a side panel attached along at least a portion of a first or second opposing longitudinal edge, an ear attached along at least a portion of the first or second opposing longitudinal edge, a disposal tape on the backsheet, or a loop tape on the backsheet comprises the microporous film having an opaque, microporous region and at least one see-through region of lower porosity within the opaque, microporous region.

7. The personal hygiene article of claim 6, wherein at least one of the topsheet or the backsheet comprises the microporous film having an opaque, microporous region and at least one see-through region of lower porosity within the opaque, microporous region.

8. The personal hygiene article of claim 6, wherein at least one of the disposal tape on the backsheet, the loop tape on the backsheet, or the acquisition layer between the topsheet and the backsheet comprises the microporous film having an opaque, microporous region and at least one see-through region of lower porosity within the opaque, microporous region.

9. A method of making the personal hygiene article of claim 1, the method comprising:
providing a microporous film;
collapsing some pores in the microporous film to form the at least one see-through region of lower porosity within the opaque, microporous region of the microporous film; and
assembling at least a portion of the microporous film including the at least one see-through region of lower porosity and the opaque, microporous region into the personal hygiene article.

10. The method of claim 9, wherein collapsing some pores in the microporous film comprises heating the microporous film to collapse the pores to form the at least one see-through region of lower porosity.

11. The method of claim 10, wherein heating the microporous film is carried out with a heated, patterned roller.

12. The method of claim 10, wherein heating the microporous film is carried out with hot air.

13. The method of claim 10, wherein heating the microporous film is carried out with a laser.

14. The method of claim 11, wherein providing the microporous film comprises stretching a film comprising the beta-nucleating agent.

15. The personal hygiene article of claim 1, wherein the personal hygiene article is a diaper or incontinence article.

16. The personal hygiene article of claim 1, wherein the personal hygiene article is a sanitary napkin.

17. The personal hygiene article of claim 1, wherein the microporous film comprises at least one of propylene homopolymer, a copolymer of propylene and other olefins, or a blend of a polypropylene homopolymer and a different polyolefin.

18. The personal hygiene article of claim 1, wherein the personal hygiene article further comprises first and second opposing longitudinal edges extending from a rear waist region to an opposing front waist region, and wherein at least one of a side panel or an ear attached along at least a portion of the first or second longitudinal edge comprises the microporous film having an opaque, microporous region and at least one see-through region of lower porosity within the opaque, microporous region.

* * * * *

UNITED STATES PATENT AND TRADEMARK OFFICE
CERTIFICATE OF CORRECTION

PATENT NO.          : 10,376,420 B2
APPLICATION NO.     : 14/897989
DATED               : August 13, 2019
INVENTOR(S)         : Neelakandan Chandrasekaran et al.

It is certified that error appears in the above-identified patent and that said Letters Patent is hereby corrected as shown below:

In the Specification

Column 11
Line 12, delete "(pseudohexangonal)," and insert -- (pseudohexagonal), --, therefor.

Column 12
Lines 23-24, delete "triphenenol" and insert -- triphenol --, therefor.
Line 31, delete "quiancridone" and insert -- quinacridone --, therefor.
Line 31, delete "-dicyclohexil-" and insert -- -dicyclohexyl- --, therefor.
Line 34, delete "antraquinone" and insert -- anthraquinone --, therefor.

Column 13
Line 17, delete "calorimetry" and insert -- Calorimetry --, therefor.

Column 14
Line 1, delete "polybuyltene" and insert -- polybutylene --, therefor.
Line 27, delete "teraphthalate" and insert -- terephthalate --, therefor.

Column 20
Line 6, delete "napthalate;" and insert -- naphthalate; --, therefor.

Column 25
Line 22, delete "that" and insert -- than --, therefor.
Line 46, delete "CHROMOPHTAL" and insert -- CROMOPHTAL --, therefor.

In the Claims

Column 28
Line 3, In Claim 14, delete "claim 11," and insert -- claim 9, --, therefor.

Signed and Sealed this
Fourteenth Day of April, 2020

Andrei Iancu
*Director of the United States Patent and Trademark Office*